(12) United States Patent
Zimmer et al.

(10) Patent No.: US 7,816,292 B2
(45) Date of Patent: Oct. 19, 2010

(54) NANO GLASS POWDER AND USE THEREOF, IN PARTICULAR MULTICOMPONENT GLASS POWDER WITH A MEAN PARTICLE SIZE OF LESS THAN 1 μM

(75) Inventors: Jose Zimmer, Ingelheim (DE); Johann Daimer, Oberkrain (DE); Matthias Rindt, Hattershaim a. M. (DE); Susanne Kessler, Ergolding (DE); Joern Besinger, Landshut (DE); Karine Seneschal-Merz, Mainz (DE)

(73) Assignee: Schott AG, Mainz (DE)

( * ) Notice: Subject to any disclaimer, the term of this patent is extended or adjusted under 35 U.S.C. 154(b) by 232 days.

(21) Appl. No.: 11/597,959

(22) PCT Filed: May 25, 2005

(86) PCT No.: PCT/EP2005/005633

§ 371 (c)(1),
(2), (4) Date: Aug. 21, 2007

(87) PCT Pub. No.: WO2005/115936

PCT Pub. Date: Dec. 8, 2005

(65) Prior Publication Data

US 2008/0044488 A1 Feb. 21, 2008

(30) Foreign Application Priority Data

May 29, 2004 (DE) .................. 10 2004 026 433

(51) Int. Cl.
C03C 3/00 (2006.01)
C03C 3/16 (2006.01)
C03C 3/076 (2006.01)
C03C 3/108 (2006.01)
C03B 37/018 (2006.01)
A01N 59/16 (2006.01)
A01N 59/14 (2006.01)
A61K 9/00 (2006.01)
A61K 9/14 (2006.01)
A61K 33/22 (2006.01)

(52) U.S. Cl. ........................ 501/11; 65/391; 65/392; 65/413; 424/489; 424/652; 424/659; 501/45; 501/55; 501/61

(58) Field of Classification Search .......... 65/391, 65/392, 413; 424/489, 652, 659; 501/11, 501/45, 55, 61

See application file for complete search history.

(56) References Cited

U.S. PATENT DOCUMENTS

| | | | | |
|---|---|---|---|---|
| 4,642,207 A | 2/1987 | Uda et al. | ................. | 264/10 |
| 5,070,045 A | 12/1991 | Comte et al. | ................. | 501/4 |
| 5,641,347 A | 6/1997 | Grabowski et al. | ............ | 106/35 |
| 5,837,025 A * | 11/1998 | Auchter-Krummel et al. | ............ | 65/21.1 |
| 5,874,684 A | 2/1999 | Parker et al. | ................. | 75/228 |
| 6,358,531 B1 | 3/2002 | Day et al. | ................. | 424/489 |
| 6,669,757 B1 | 12/2003 | Lough | ................. | 75/743 |
| 2003/0064532 A1 | 4/2003 | Chen | ................. | 483/3 |
| 2003/0148282 A1 | 8/2003 | Mirkinet et al. | ................. | 435/6 |
| 2003/0234978 A1 | 12/2003 | Garito et al. | ................. | 359/341.5 |
| 2004/0042953 A1 | 3/2004 | Kim et al. | ................. | 423/440 |
| 2004/0052957 A1 | 3/2004 | Cramer et al. | ................. | 427/197 |
| 2004/0067208 A1 | 4/2004 | Lennon et al. | ................. | 424/59 |
| 2004/0253321 A1 * | 12/2004 | Fechner et al. | ................. | 424/642 |

FOREIGN PATENT DOCUMENTS

| | | |
|---|---|---|
| DE | 1022009 | 1/1958 |
| DE | 43 23 143 | 12/1994 |
| DE | 44 43 173 | 7/1996 |
| DE | 195 20 448 | 12/1996 |
| DE | 69600059 | 2/1998 |
| DE | 199 07 038 | 8/2000 |
| DE | 10322444 A1 * | 10/2003 |
| DE | 103 45 625 | 4/2005 |
| EP | 0997132 | 5/2000 |
| JP | 61-186248 * | 8/1986 |
| JP | 04067868 * | 3/1992 |
| WO | WO 00/12347 * | 3/2000 |
| WO | WO 00/12437 * | 3/2000 |
| WO | WO 01/03650 | 1/2001 |
| WO | WO 01/04252 | 1/2001 |
| WO | WO 03/018495 | 3/2003 |
| WO | WO 03/018496 | 3/2003 |

(Continued)

OTHER PUBLICATIONS

Hawley's Condensed Chemical Dictionary, Thirteenth edition, John Wiley & Sons, Inc.: New York, 1997, pp. 537.*

(Continued)

Primary Examiner—Johann R Richter
Assistant Examiner—James H Alstrum Acevedo
(74) Attorney, Agent, or Firm—Ohlandt, Greeley, Ruggiero & Perle, L.L.P.

(57) ABSTRACT

A glass powder or a glass-ceramic powder is provided that includes multicomponent glasses with at least three elements, where the glass powder or a glass-ceramic powder has a mean particle size of less than 1 μm. In some embodiments, the mean particle size is less than 0.1 μm, while in other embodiments the mean particle size is less than 10 nm.

10 Claims, No Drawings

FOREIGN PATENT DOCUMENTS

| WO | WO 03/018498 | 3/2003 |
| WO | WO 03/018499 | 3/2003 |
| WO | WO 03/050052 | 6/2003 |
| WO | WO 03/059834 | 7/2003 |
| WO | WO 03/062163 | 7/2003 |
| WO | WO 2004/024100 | 3/2004 |

OTHER PUBLICATIONS

Clasen, Rolf, *High-purity glasses and ceramics prepared by sintering compacts of nanosized, Particles: advantages and perspectives*, Key Engineering Materials Trans Tech Publications, Switzerland, pp. 235-238, 2002.

Guardani et al., *Production of sub-micron glass spheres from immiscible glass phases*, Physics and Chemistry of Glasses, Society of Glass Technology, Sheffield, Great Britain, pp. 22-24, 1996.

Junge et al., *Elektronik*, VCH Publishers, pp. 89-90, 1993 (no English translation).

Wu et al. *Preparation of nanoscale Li20-A1203-Si02*, Transactions of the Nonferrous Metals, Society of China, pp. 80-83, 2003.

*Database WPI* (XP002357331), Derwent Publications, including CN 1361076 (original patent and English abstract included) as cited in the International Search Report dated Dec. 14, 2005 based on PCT/EP2005/005633.

International Search Report dated Dec. 14, 2005 based on PCT/EP2005/005633.

* cited by examiner

NANO GLASS POWDER AND USE THEREOF, IN PARTICULAR MULTICOMPONENT GLASS POWDER WITH A MEAN PARTICLE SIZE OF LESS THAN 1 μM

The subject of the invention is multicomponent glasses containing at least three (3) elements with a mean particle size of less than 1 μm, preferably less than 0.1 um, particularly preferred of less than 10 nm. Glasses with these mean particle sizes are also denoted nanopowders. In addition to multicomponent glasses, the Application also comprises a method for the production of such glasses as well as the use thereof.

Inorganic nanopowders are known for noncrystalline compositions of $SiO_2$ and for crystalline compositions, such as, e.g., $TiO_2$ or ZnO. With respect to $SiO_2$ nanopowder, refer to the product Aerosil® of Degussa.

In addition, CeO nanoparticles are known for polishing suspensions, e.g., of the Nanophase company (USA) as well as $ZrO_2$ nanoparticles or $Al_2O_3$ nanoparticles of the Nanogate company (Germany).

Metal nanoparticles are known, e.g., for silver and silver alloy. Such nanoparticles are utilized, for example, as antimicrobial active substances, e.g., for polymers.

Powders of metal nanoparticles may also be utilized for bonding in the field of electronics. According to H. D. Junge, A. Möschwitz, "Elektronik", VCH Publishers 1993, p. 89, bonding is a soldering process for the contacting of electronic components, for example, on an integrated circuit. Bonding temperatures are greatly reduced by the use of metal nanopowders.

In addition to the above-named nanoparticles, hydroxyapatite nanoparticles, for example, of the BASF company (Germany) have become known, which are used in the fields of oral hygiene, dental hygiene, i.e., in the field of oral care applications.

Proceeding from the above-described prior art, ceramic nanoparticles containing 2 elements, usually consisting of a metal and oxygen, have primarily become known.

Two-element systems consisting of a single component, namely pure $SiO_2$ particles, have become known exclusively as nanoparticles in the vitreous phase. A disadvantage of such pure $SiO_2$ systems is that they have no particularly broad variation in material properties due to their small chemical variability. This concerns, in particular, optical, chemical, physical and mechanical properties.

Glasses with a bioactive effect and also in part an antimicrobial effect are described as bioglass by L. L. Hensch, J. Wilson, An Introduction to Bioceramics, World Scientific Publ. 1993. Such bioglass is characterized by the formation of hydroxyapatite layers in aqueous media. Alkaline and alkaline-earth silicate glasses that are devoid of heavy metals and have antimicrobial properties are described in the Applications WO 01/04252 and WO 01/03650.

Glasses with antimicrobial effectiveness have become known from the following Patent Applications: WO 03/018495, WO 03/18498, WO 03/18499, WO 03/050052, WO 03/062163, WO 03/018496. The glass powders described in these publications were obtained by grinding, for example, in aqueous media. As described in the above publications, glass powders with a mean particle size that corresponds to that of nanoparticles, cannot be obtained by a grinding.

Glasses that find use in the dental field, so-called dental glasses, have become known from DE 4,323,143; U.S. Pat. No. 5,641,347; DE 4,443,173 and EP 0997132.

Glasses and glass ceramics, in particular, which are characterized by a slight expansion or even by no expansion, are shown in DE 19907038 and U.S. Pat. No. 5,070,045.

The nanoparticles known from the prior art are utilized in a plurality of fields. For example, the application of nanoparticles in cosmetic sunscreen formulations is described in US 2004-0067208.

The surface treatments of nanoparticles as well as the printing thereon are described in US 2004-0052957.

The production of nanoparticles as well as scratchproof coatings containing nanoparticles is described in DE 0001022009 A1.

DE 000069600059 describes the use of $TiO_2$ nanoparticles in sunscreen agents.

US 2004-0042953 describes the use of nanoparticles in WC powders, wherein the mean particle size fluctuates between 10 and 20 nm. These nanoparticles are produced via gas-phase reactions.

The use of nanoparticles for the detection of nucleic acids has become known from US 2003-0148282.

US 2003-0064532 describes the use of semiconductor nanoparticles in the field of luminescence and optical data storage.

The production, for example, of silver or silver alloy nanopowders is carried out by means of PVD methods.

For example, a PVD plasma arc method for the production of nanoparticles via vaporization and condensation has become known from U.S. Pat. No. 4,642,207.

A method for the production of nanocrystalline material also has become known from U.S. Pat. No. 5,874,684. Binary oxides are utilized as raw materials for this. Different atmospheres may be used for the production of different substances.

The object of the invention is to provide a multicomponent glass powder, which is characterized in that it can be used in a plurality of fields and has an improved activity when compared with conventional glass powders.

The object is accomplished by a glass powder which has multicomponent glasses containing at least 3 elements, wherein the mean particle size of the glass powder is less than 1 μm, preferably less than 0.1 μm, still more preferably less than 50 nm, particularly preferred less than 10 nm.

In a preferred embodiment, the glass contains more than 4 elements, particularly preferred more than 5, and most particularly preferred, more than 6 elements.

Oxide components, thus, for example, $SiO_2$ or $B_2O_3$ are understood as components of an oxide glass in this Application. The individual element, thus Si or B or O is to be understood as the element in a glass composition. A multicomponent glass is thus a glass which comprises $SiO_2$ and $B_2O_3$, for example, as components. A glass which comprises $SiO_2$ and $B_2O_3$ has a total of three elements. Thus, one would speak of a 2-component glass containing 3 elements in this Application.

According to the invention, glass powders with a particle size of less than 1 μm, which are also named nanoglasses, comprise $SiO_2$ and/or $B_2O_3$ and/or $P_2O_5$ as network formers. The proportion of network formers or the sum of the network formers, if the multicomponent glass comprises more than one network former, lies preferably between 30 and 95 wt. %, more preferably between 30 and 80 wt. %, in particular between 40 and 75 wt. %, and most preferably between 50 and 70 wt. %. Depending on the principal network former, the glasses can be classified into groups of silicate, borate or phosphate glasses.

Alkali ions, such as, e.g., Na, K, Li, Cs, may be introduced into the glass composition as network modifiers. The concentration of alkalis lies in all between 0 and 50 wt. %, preferably between 0 and 30 wt. %. The alkalis may also serve for adjusting the reactivity of the glass, since the glass network can be interrupted in a targeted manner by alkalis. For example, biocide ions introduced into the glass matrix, such as, e.g., Zn or Ag, can be easily delivered.

In addition to or instead of alkalis, alkaline-earth ions, such as, e.g., Mg, Ca, Sr, Ba, can be present in total between 0 and 50 wt. %. The alkaline-earth ions also act as network modifiers and serve for adjusting the reactivity of the glass. Ca takes on a special role. A mineral layer can be formed on the particle surface in aqueous media, the so-called hydroxyapatite layer, due to the presence of Ca in the case of special bioactive glasses. In addition, the multicomponent glasses may additionally comprise aluminum oxide. Aluminum oxide considerably affects the chemical stability as well as the crystallization stability of the glasses. The $Al_2O_3$ concentration lies preferably between 0 and 25 wt. %.

In addition to the network components, the glass may comprise zinc oxide as an essential component of the glass. The Zn ions of the glass may be released and lead to an antimicrobial action, which is further supported by alkali or alkaline-earth ions. The ZnO concentration usually is between 0-25 wt. % in the initial composition of raw materials. Zinc can also improve the chemical stability of the glasses.

The multicomponent glasses may also comprise titanium oxide and/or zirconium oxide. The refractive index of the glass powder can be adjusted in a targeted manner by means of these additives. The addition of $TiO_2$ may also be utilized particularly for UV blocking.

If the nanopowders are glass ceramic nanopowders, additives of $TiO_2$ or $ZrO_2$ can serve as nucleation agents.

In addition, an adjustment of the chemical stability of nanopowders is possible with $TiO_2$ or $ZrO_2$.

The hydrolytic stability may be improved, in particular, by the addition of $ZrO_2$, which is of particular importance in the case of hygroscopic nanopowders. In addition to adjusting the refractive index, $TiO_2$ and $ZrO_2$ may also be used for adjusting the E-modulus.

The concentration of $TiO_2$ preferably lies between 0 and 25 wt. % and the concentration of $ZrO_2$ lies between 0 wt. % and 30 wt. %.

The nanoglass powder may comprise tantalum oxide and/or tungsten oxide for the fine adjustment of the refractive index.

In addition to or instead of Zn, the glass may contain Ag, Cu, I in order to achieve antimicrobial effectiveness. In sum total, the concentration of $Ag_2O$, CuO, ZnO, I is less than 15 wt. %, preferably less than 10, and most preferably less than 5 wt. %.

Noble metals such as Au, Pt may also be contained in metal or oxide form at less than 10 wt. %, preferably less than 5 wt. %, most preferably less than 2 wt. %.

Color-rendering ions such as, e.g., Cr, Mn, Ni, V, Ce, Fe, V, Co may be present in total (oxide) of up to 10 wt. %.

Rare-earth ions such as, e.g, Eu, Ce, Sm, Nd, Er, Sm, Yb may be introduced as dopants in the usual concentrations.

Fluorine can be contained in the glasses as a melting adjuvant.

Oxides of the elements Nb, La, Pb and Bi serve primarily for adjusting the refractive index or dispersion.

The addition of elements such as, e.g., Ba, Cs, La makes it possible to adjust a high radio opacity.

Refining agents, such as, e.g., SnO, $As_2O_3$, $Sb_2O_3$ may also be contained in the usual concentrations in the nanoglass powders, with the exception of nanoglasses which find use in dental, medical and cosmetic applications.

The above-mentioned metals Au, Ag, Pt, Cu may be present not only in oxide form, but also as metals in the glass matrix.

Radioactive elements may also be added.

In special embodiments, nitrides or oxide-nitrides may also be used as initial materials and the corresponding nitride or oxide-nitride nanoglasses can be obtained. Of advantage in nitride or oxide-nitride nanoglasses are the better mechanical properties than those found in oxide glasses.

As indicated above, the nanopowders according to the invention have mean particle sizes of less than 1 μm, preferably less than 200 nm, particularly preferred of less than 100 nm, still more preferably less than 50 nm, and most preferably less than 20 nm. In a particular embodiment, particle sizes of less than 5 nm are used. In special embodiments, the nanoparticles can be smaller than 2 nm.

The BET surface of conventional inorganic fillers in dental materials lies, e.g., between 4 and 65 $m^2/g$.

In contrast to this, the BET surfaces of nanoparticles are larger than 50 $m^2/g$, preferably larger than 100 $m^2/g$, still more preferably larger than 500 $m^2/g$, and most preferably larger than 900 $m^2/g$.

Due to the high surface-to-volume ratios in the nanoglasses according to the invention, the surface properties play an increasingly large role in comparison to the bulk properties. Due to the large free surface, for the person skilled in the art, even in the case of glasses that are inert in and of themselves, such as antimicrobial silicate glasses, surprisingly high reactivity is attained, in particular a high ion delivery, e.g., in aqueous media or in organic compounds, and a high antimicrobial effect of the powder is obtained.

The particles can be used as a powder and as a suspension.

Amorphous, phase-separated, crystallized glass or glass ceramic nanoparticles may be utilized. Different phases may be attained beforehand in the primary production process or later in a post-processing.

For use as a filler in the dental field, a modification of the surface with organosilanes, such as, e.g., methacryloxypropyltrimethoxysilane, is possible and advantageous.

The organosilanes used are characterized particularly by the fact that they can bind both to the glass surface as well as also to an organic resin by means of an organic functional side group. In this way, on the one hand, formulation in the organic resin matrix is facilitated and, on the other hand, the mechanical stability is increased. 3-Methacryloxypropyltrimethoxysilane, which is better known under the tradename MEMO of Degussa, is the most widely used for dental applications. In addition, there is a plurality of other functional side groups, such as, for example, amino, glycidoxyl, mercapto, vinyl, allyl groups with the corresponding spacers.

Ions of the elements La, Ba, Sr, Y, Yb, Nb, Zr, Zn serve for adjusting the x-ray visibility of dental glasses.

The nanopowders according to the invention, comprising multicomponent glasses and glass ceramics can be used in the fields of cosmetics, e.g., as UV blockers for UV-A and/or UV-B, for dental fillers, oral care, for optical polymers, for sintering materials, in antimicrobial applications, in the medical field as an active ingredient or as a support for active ingredients, for water filtering, water purification, water treatment, as glass solders; as pigments, for rapid prototyping, which describes the very rapid production of three-dimensional structures, in fuel cells, as abrasive materials, for catalysis, as UV screens, in polishing processes, in textile fibers, in thermoplasts, in coloring materials and paints; in surface technology, as simple-to-refine, antibonding, antiscratching, antireflecting, antitarnishing films, for corrosion protection; in the field of ceramic technologies, as raw materials, e.g., for glasses or as glass ceramics, for crystal production, for the production of optical glass ceramics and optical ceramics as well as optical polymers, in laser technology, in printing technology, in biotechnology, as fluorescent markers, as luminescent material, as adhesives, in polymers (e.g., duromers, plastomers, monomers), as contact lenses in foils, printing paper; illuminants, copier technology, membranes.

Another application represents the use of nanoglasses in the field of electronics, for example, as glass solders for joining or as passivation glass for semiconductor components.

The production of nanoparticles takes place, for example, by a PVD (Physical Vapor Deposition) method. The PVD methods describe a vaporization technique. With respect to such PVD methods, refer to H. D. Junge and G. Müller, VDI-Lexikon Elektrotechnik, 1994, p. 26 to 27 or VDI-Lexikon "Werkstofftechnik" [Material Techniques] VDI Publishers, 1993, pp. 810 to 811 and pp. 5 to 6. The disclosure content of these documents is incorporated to the full extent in the present Application. For PVD methods, all substances of the glass are vaporized in a plasma. The vaporized substances are deposited on a cold surface, for example, a substrate surface and are newly organized in the vitreous state. Multicomponent nanoparticles of glass or glass ceramics according to the invention are formed. As described previously, in addition to nanoglasses, a nanoglass ceramic or a nanoglass that comprises a separated system can also be produced in this way. It is also possible to subsequently subject nanoglasses produced in this way to a ceramization. Also, the production of nanoparticles is possible by means of the sol-gel method.

In addition to the described PVD methods, the CVD methods may also be used. CVD (Chemical Vapor Deposition) methods describe chemical precipitation from the gas phase. With respect to CVD methods, refer to the VDI-Lexikon "Werkstofftechnik" [Material Techniques] VDI Publishers 1993, p. 139 and pp. 5 to 6, the disclosure content of which is incorporated to the full extent in the disclosure content of the present application.

Another method for the production of nanoparticles is flame pyrolysis. Reactive gases are guided into a flame in flame pyrolysis. The nanoparticles are synthesized in the flame and deposited in cold regions. Liquid raw materials can also be used in addition to gaseous raw materials for flame pyrolysis.

If a nonoxide carrier gas is utilized in the described methods, in particular in PVD methods, then nitride or oxynitride nanoglasses can be produced.

The above-described PVD methods are most particularly suitable for the production of the described nanoglasses or nanoglass ceramics. In the case of PVD methods, plasma methods are particularly suitable, in particular, plasma methods combined with high-frequency vaporization or electron vaporization. Plasma methods are characterized by the fact that the vaporization of the raw material takes place in a plasma.

Metals or metal oxides are used as the initial materials in the PVD methods known in the prior art.

Particularly preferred for use as initial materials for the production of the multicomponent glasses according to the invention, however, are glasses that are already multicomponent glasses with particle sizes of less than 1 µm. If multicomponent glasses are used as initial materials, then different multicomponent glasses can be mixed in different parts by weight and particle size distributions.

By the use of multicomponent glasses as raw materials, suitable element combinations can already be combined in the raw material. In the PVD method, by local heating of the multicomponent glass as the raw material, this raw material is selectively vaporized and the raw materials then are deposited again as the glass powder or glass ceramic powder according to the invention with particle sizes of less than 1 µm. As described, the initial materials are introduced, for example, in bar or powder form into a vessel, and are there vaporized in a plasma arc and then the corresponding nanoparticles are deposited in a current of gas.

The advantage of the PVD method is that, due to the rapid cooling rates, glasses that are sensitive to crystallization can even be deposited in amorphous form. This also applies to glasses that cannot be stably produced under standard melting conditions and for which amorphous glass powder thus cannot be obtained via conventional fusion and grinding.

Surface modifications as well as modifications of the total composition can be obtained by introducing different reaction gases. For example, oxide glasses can be deposited by means of oxide carrier gases, while, for example, oxynitride glasses can be deposited by means of non-oxide carrier gases.

Because of their very small particle size, the glasses according to the invention can be used for bridging over gaps in the bonding method or as adhesive compounds in optical applications, for UV or IR absorption, for heat insulation, for light reflection, as a fire-resistant material, as a sealant, as a glossy material, as a brilliant color material, as well as in electrostatics.

Other fields of application are porous electrodes for fuel cells, hard solders for ceramic-metal compounds or low-temperature solders. Here, in particular, solders in the field of glass-glass, glass-metal, glass-ceramic or glass-crystal compounds.

In addition, in general, glasses, ceramics, glass ceramics, crystals, metals can be combined with one another with such solders.

Nanoparticles according to the invention can also be deposited electrophoretically onto surfaces or into porous objects.

The inorganic, non-metal biocides described in the prior art can only be produced and utilized in relatively large particle sizes of more than 1 µm. Therefore, they have a lower effectiveness than organic biocides.

Surprisingly, the reactivity, but in particular the antimicrobial effectiveness can be increased to an unusually great extent by the nanoparticles according to the invention. Here, not only the greater availability of the incorporated active substance, such as, e.g., Ag, Zn, Cu, plays a role, but also the glass surface itself with a corresponding zeta potential or locally high pH values. The increased surface generates an additional, synergistic antimicrobial effect. In contrast to metal antimicrobial nanopowders, for example, silver nanopowder, there is the advantage that oxide compounds have a smaller tendency to become discolored and the silver is already present in its antimicrobially effective oxidized form. The glass or glass ceramic nanoparticles can be adjusted by their composition in such a way that they completely dissolve in aqueous systems.

If nanopowders are obtained according to the invention from null expansion materials, then they are suitable particularly for sintering and as a filler. In particular, it is possible to produce null-expansion formed objects via the sintering route, by means of sintering such nanopowders. By means of the nanoparticles according to the invention, it is possible to reduce the sintering temperature and to obtain very high final densities with very low porosity, and these particles are characterized by a small scatter and high transparency.

Optical glasses may also be obtained from the nanoparticles according to the invention by viscous sintering.

The nanoglasses are combined into a sintered compact. Based on the composition of the sintered compact made of a plurality of individual nanoparticles, an extremely large surface is introduced into the sintered compact. And because of this extremely large surface, special structures can be produced with minimum crystallite sizes. The crystallization of the sintered compact can be both surface-controlled or volume-controlled, each time depending on the type of glass. Another advantage of the extremely large surface of the compact is that nanocrystals are produced in the sintered solid materials (both in the volume as well as in surface-controlled crystallization). This is a way to produce sintered glass ceramics with nanocrystals.

Nanoglass powders can be utilized also as sintering aids for high-melting materials due to the high surface reactivity. Another application is their use for melting point-sensitive materials or semifinished products. The soldering temperature can be reduced here with the help of the surface reaction that takes place at an early time.

Soldering glasses made of nanoparticles, in particular in combination with laser sintering or laser soldering are used in order to obtain temperature and stress loads that are as low as possible.

Another advantage of the nanoglasses according to the invention lies in the fact that in contrast to crystalline ceramic nanoparticles, glasses can be adjusted in a wide range in their optical layers. This possibility of adjustment involves transmission, refractive index, dispersion, and also partial dispersion of the glass, for example. By means of mixtures of polymers with nanoglasses, it is possible to obtain polymer-glass composites, in which the optical parameters can be very precisely adjusted. Due to the variability of glass chemistry and corresponding surface modifications which are conducted during and after production, properties such as the dispersability may also be adjusted. This is necessary, e.g., if nanoparticles are dispersed in monomers.

Since, due to the small particle size of the nanoparticles, a very high degree of filling of up to more than 50 wt. % can be introduced into monomers, without influencing the viscosity of the monomer, by the use of nanopowders of a glass that is adapted to the application, for example, in its refractive index, a highly filled polymer with only a slight shrinkage during polymerization can be produced. In highly filled polymers, optical effects, for example a Tyndall effect, can then be produced or else avoided in a targeted manner.

It is possible with the use of colored glasses to then also color polymers, if common commercial ceramic pigments cannot be used and organic dyes will not be used for reasons either of toxicology or of chemical, thermal or UV resistance.

Another field of application of the nanoglass powders according to the invention is so-called rapid prototyping, i.e., the production of three-dimensional prototypes, for example, in the field of tissue engineering, thus the production of three-dimensional implant scaffoldings that serve as support materials for the growth of tissue cells.

Due to their high biocompatibility, nanoglass powders or nanoglass ceramic powders can also be utilized as implant material, coating material for implants or vehicle systems for medications. Due to the inflammation-inhibiting or antimicrobial properties, the nanoglasses or the nanoglass powders according to the invention can also be used directly as an active substance.

Alternatively, it is possible to introduce active substances into the glass or to apply active substances onto the glass surface. Such systems then represent so-called "release systems".

Composite materials, e.g., of LGA and/or PGA or their copolymers can be used for biomaterial, in particular for tissue engineering. LGA and PGA are bioresorbable polymers.

Use of the nanoparticles according to the invention in the cosmetic field is possible. In particular, for application in the cosmetic field, a UV-blocking and/or a light-scattering effect can be developed.

The production of glass nanoparticles and/or glass ceramic nanoparticles according to the invention that contain antioxidative, inflammation-inhibiting, antimicrobial, remineralizing effects is also possible. If specific substances are added, then it is possible to produce magnetic nanoparticles, for example, for treatments that promote blood circulation.

Since the chemical composition of the glasses can be varied, it is possible to adjust and match the mechanical properties of the nanoparticles of glass or glass ceramics, such as, e.g., hardness, E-modulus, density, chemical resistance (e.g., to water, alkaline solutions and acids), or the electrical properties. In addition to the particle size, the zeta potential can also be matched by modifications of the composition and/or the surface.

The invention will be described in more detail below on the basis of embodiment examples.

Compositions of glasses or initial glasses for glass ceramics from which nanoglass particles or nanoglass ceramic particles can be produced by the method according to the invention are given in wt. % in Table 1.

For example, in the PVD method, the indicated glass compositions according to Table 1 refer to the glass compositions of the initial glasses, which can be vaporized, for example, by means of an electron beam. The glass composition of the nanoglass particles or nanoglass ceramic particles deposited in the PVD method corresponds essentially to the compositions of the initial glasses with an appropriate conduction of the method.

TABLE 1

| | Glass compositions | | | | | | | | | |
|---|---|---|---|---|---|---|---|---|---|---|
| | Example | | | | | | | | | |
| | 1 | 2 | 3 | 4 | 5 | 6 | 7 | 8 | 9 | 10 |
| $SiO_2$ | 45 | 65 | 73.5 | 50.4 | 93 | 80 | 5 | 5 | | 45 |
| $B_2O_3$ | | 15 | 10.0 | 13.4 | | | 50 | 20 | | |
| $P_2O_5$ | 5 | | | | | | | | 55 | 5 |
| $Na_2O$ | 25 | 17 | 6.6 | 0.1 | | | 10 | | 2.5 | 24 |
| $Li_2O$ | | | | | | | | | 2.5 | |
| $K_2O$ | | | 2.6 | | | | | | 2 | |
| CaO | 25 | | 0.6 | | | | | | | 24 |
| MgO | | | | | | | 5 | | | |
| SrO | | | | 0.3 | | | | | | |
| BaO | | | | 24.0 | | | | | | |
| $Al_2O_3$ | | 1 | | 6.7 | 11.8 | | | | 3 | |
| $TiO_2$ | | | | | | 7 | | 2.5 | | 2 |
| $ZrO_2$ | | | | | | | 20 | 2.5 | | |
| ZnO | | | | | | | | 20 | 35 | |
| $La_2O_3$ | | | | | | | | 35 | | |
| $WO_3$ | | | | | | | | 5 | | |
| $Nb2O5$ | | | | | | | | 10 | | |
| PbO | | | | | | | | 30 | | |
| $Ag_2O$ | | 2 | | | | | | | | |

Common refining agents in this Application are understood to be, for example, the refining agents $Sn_2O_3$, NaCl, $As_2O_3$, $Sb_2O_3$, $As_2S_3$, $Sb_2S_3$; 0-4 wt. % of the total composition is understood as the usual quantity of a common refining agent.

Embodiment examples of nanoglass powders and their use will be given in the following.

Embodiment Example 1 refers to a nanoglass powder, which is introduced into a polymer matrix and leads to an antimicrobial effect of the polymer-nanoglass composite material. According to Embodiment Example 1, 0.1 wt. % nanoglass powder with a particle size of less than 1 μm according to Example 2 in Table 1 is worked into a polystyrene matrix and extruded into plates. The antimicrobial effectiveness of the surface is tested according to ASTM standard. A reduction of the test pathogens (*E. coli, Candida albicans*) by more than 2 log units is determined.

According to Embodiment Example 2, a 0.1 wt. % bioactive nanoglass powder with particle sizes of less than 1 nm according to Example 1 in Table 1 is worked into a formulation for a deodorant. A significant reduction in perspiration is observed.

In Embodiment Example 3, 50 wt. % of the nanoglass powder according to the invention is formulated into a dental resin. Typical dental resins are described in EP 04 75,239 and documents cited therein. The nanoglass of the glass powder has a glass composition according to Example 4 in Table 1. The mean particle size is smaller than 1 μm.

In Embodiment Example 4, a high-melting glass (e.g., Schott glass of Number 8330) is mixed with nanopowder as an admixture in order to reduce the sintering temperature.

Embodiment Example 5 involves a glass solder, comprised of 70 vol. % nanoglass powder with a composition according to Example 9 in Table 1 and a particle size of <1 μm and 30 vol. % of an inert filler (e.g. cordierite) for adapting to expansion. The composite nanoglass solder obtained in this way has a melting point that is 50° C. lower when compared to the same mixture of original material.

Embodiment Example 6 involves a polymer-glass composite, in which a fluoropolymer is mixed each time with 5, 10, 20 wt. % of a nanopowder, which has the glass composition of a lead silicate glass with a refractive index of n=1.9. Depending on the proportion of nanopowder in the fluoropolymer in each case, the refractive index of the composite material is shifted to higher values.

In Embodiment Example 7, 5 wt. % of a nanoglass powder with particle sizes of less than 1 μm with a glass composition that comprises 2 wt. % $TiO_2$ is added to a sunscreen formulation in order to obtain a UV blocking.

The invention claimed is:

1. A method of manufacturing a multi-component glass or glass ceramic powder in the form of nanoparticles, comprising:
   providing at least three initial glass forming materials;
   vaporizing all of the initial glass forming materials in a plasma to form vaporized components; and
   depositing the vaporized components on a substrate so that the vaporized components are organized in a vitreous state or in an amorphous form, which has a composition comprising 5 to 55 weight percent based on oxide of $P_2O_5$, 20 to 35 weight percent based on oxide of ZnO, and at least one initial glass forming material selected from the group consisting of 0.1 to 25 weight percent based on oxide of $Na_2O$, 2.5 weight percent based on oxide of $Li_2O$, 2 to 2.6 weight percent based on oxide of $K_2O$, and 1 to 11.8 weight percent based on oxide of $Al_2O_3$.

2. The method according to claim 1, wherein the step of providing at least three initial glass forming materials comprises providing glasses that are already multi-component glasses with particle sizes of less than 1 μm.

3. The method according claim 1, wherein the multi-component glass or glass ceramic powder has a mean particle size of less than 200 nm.

4. The method according to claim 1, wherein the multi-component glass or glass ceramic powder comprises particles having a surface area that is larger than 50 $m^2$/g as determined by the BET method.

5. A method of manufacturing a multi-component glass or glass ceramic powder in the form of nanoparticles, comprising:
   providing at least three initial glass forming materials;
   vaporizing all of the initial glass forming materials in a plasma to form vaporized components; and
   depositing the vaporized components on a substrate so that the vaporized components are organized in a vitreous state or in an amorphous form, which has a composition comprising 10 to 50 weight percent based on oxide of $B_2O_3$, 5 to 80 weight percent based on oxide of $SiO_2$, and PbO.

6. The method according to claim 5, wherein the sum of $SiO_2+B_2O_3+P_2O_5$ is more than 25 weight percent.

7. The method according to claim 5, wherein the step of providing at least three initial glass forming materials comprises providing glasses that are already multi-component glasses with particle sizes of less than 1 μm.

8. The method according claim 5, wherein the multi-component glass or glass ceramic powder has a mean particle size of less than 200 nm.

9. The method according to claim 5, wherein the multi-component glass or glass ceramic powder comprises particles having a surface area that is larger than 50 $m^2$/g as determined by the BET method.

10. The method according to claim 5, wherein the composition comprises 40 to 80 weight percent based on oxide of $SiO_2$ and 13.4 to 50 weight percent based on oxide of $B_2O_3$.

* * * * *